US00PP26444P2

(12) United States Plant Patent
Kanaya et al.

(10) Patent No.: US PP26,444 P2
(45) Date of Patent: Mar. 1, 2016

(54) ***CALIBRACHOA* PLANT NAMED 'SUNBEL 789'**

(50) Latin Name: ***Calibrachoa* sp.**
Varietal Denomination: Sunbel 789

(71) Applicants: Takeshi Kanaya, Chiba (JP); Kiyoshi Miyazaki, Shiga (JP); Yasuyuki Murakami, Shiga (JP)

(72) Inventors: Takeshi Kanaya, Chiba (JP); Kiyoshi Miyazaki, Shiga (JP); Yasuyuki Murakami, Shiga (JP)

(73) Assignee: Suntory Flowers LTD., Tokyo (JP)

( * ) Notice: Subject to any disclaimer, the term of this patent is extended or adjusted under 35 U.S.C. 154(b) by 227 days.

(21) Appl. No.: 13/998,616

(22) Filed: Nov. 15, 2013

(51) Int. Cl.
*A01H 5/02* (2006.01)

(52) U.S. Cl.
USPC ..... Plt./413

(58) Field of Classification Search
USPC ..... Plt./413
See application file for complete search history.

*Primary Examiner* — Anne Grunberg
(74) *Attorney, Agent, or Firm* — C. A. Whealy

(57) ABSTRACT

A new and distinct cultivar of *Calibrachoa* plant named 'Sunbel 789', characterized by its compact and mounding plant habit; vigorous growth habit; freely branching habit; early and freely flowering habit; long flowering period; white-colored flowers with yellow-colored throats; and good garden performance.

1 Drawing Sheet

Botanical designation: *Calibrachoa* sp.
Cultivar denomination: 'SUNBEL 789'.

BACKGROUND OF THE INVENTION

The present invention relates to a new and distinct cultivar of *Calibrachoa* plant, botanically known as *Calibrachoa* sp. and hereinafter referred to by the name 'Sunbel 789'.

The new *Calibrachoa* plant is a product of a planned breeding program conducted by the Inventors in Higashiomi, Shiga, Japan. The objective of the breeding program is to develop new compact, mounding and freely branching *Calibrachoa* plants with numerous large and attractive flowers.

The new *Calibrachoa* plant originated from a cross-pollination conducted by the Inventors in Higashiomi, Shiga, Japan in June, 2010 of a proprietary selection of *Calibrachoa* sp. identified as code number 10C224, not patented, as the female, or seed, parent with a proprietary selection of *Calibrachoa* sp. identified as code number 8711-1, not patented, as the male, or pollen, parent. The new *Calibrachoa* plant was discovered and selected by the Inventors as a single flowering plant from within the progeny of the stated cross-pollination in a controlled greenhouse environment in Higashiomi, Shiga, Japan in August, 2011.

Asexual reproduction of the new *Calibrachoa* plant by vegetative cuttings in a controlled greenhouse environment in Higashiomi, Shiga, Japan since August, 2011 has shown that the unique features of this new *Calibrachoa* plant are stable and reproduced true to type in successive generations.

SUMMARY OF THE INVENTION

Plants of the new *Calibrachoa* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunbel 789'. These characteristics in combination distinguish 'Sunbel 789' as a new and distinct *Calibrachoa* plant:

1. Compact and mounding plant habit.
2. Vigorous growth habit.
3. Freely branching habit.
4. Early and freely flowering habit.
5. Long flowering period.
6. White-colored flowers with yellow-colored throats.
7. Good garden performance.

Plants of the new *Calibrachoa* can be compared to plants of the female parent selection. Plants of the new *Calibrachoa* differ primarily from plants of the female parent selection in the following characteristics:

1. Plants of the new *Calibrachoa* are more compact than plants of the female parent selection.
2. Plants of the new *Calibrachoa* are more mounding than and not as trailing as plants of the female parent selection.

Plants of the new *Calibrachoa* can be compared to plants of the male parent selection. Plants of the new *Calibrachoa* differ primarily from plants of the male parent selection in flower color as plants of the male parent selection have pink-colored flowers.

Plants of the new *Calibrachoa* can also be compared to plants of *Calibrachoa* sp. 'Suncalho', disclosed in U.S. Plant Pat. No. 21,810. In side-by-side comparisons conducted in Higashiomi, Shiga, Japan, plants of the new *Calibrachoa* and 'Suncalho' differed primarily in the following characteristics:

1. Plants of the new *Calibrachoa* had smaller leaves than plants of 'Suncalho'.
2. Plants of the new *Calibrachoa* flowered earlier than plants of 'Suncalho'.
3. Plants of the new *Calibrachoa* were more freely flowering than plants of 'Suncalho'.

4. Plants of the new *Calibrachoa* had smaller flowers than plants of 'Suncalho'.
5. Plants of the new *Calibrachoa* had smaller sepals than plants of 'Suncalho'.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph at the top of the sheet comprises a side perspective view of a typical flowering plant of 'Sunbel 789' grown in a container.

The photograph at the bottom of the sheet is a close-up view of a typical flowering plant of 'Sunbel 789'.

DETAILED BOTANICAL DESCRIPTION

The aforementioned photographs and following observations, measurements and values describe plants grown during the late summer in 15-cm containers in an outdoor nursery in Higashiomi, Shiga, Japan and under cultural practices typical of commercial *Calibrachoa* production. During the production of the plants, day temperatures averaged 23° C. and night temperatures averaged 13° C. Plants were four months old when the photographs and the description were taken. In the following description, color references are made to The Royal Horticultural Society Colour Chart, 2007 Edition, except where general terms of ordinary dictionary significance are used.

Botanical classification: *Calibrachoa* sp. 'Sunbel 789'.

Parentage:

*Female, or seed, parent*.—Proprietary selection of *Calibrachoa* sp. identified as code number 10C224, not patented.

*Male, or pollen, parent*.—Proprietary selection of *Calibrachoa* sp. identified as code number 8711-1, not patented.

Propagation:

*Type*.—By vegetative cuttings.

*Time to initiate roots, summer*.—About one week at temperatures about 15° C. to 20° C.

*Time to produce a rooted young plant, summer*.—About three weeks at temperatures about 15° C. to 20° C.

*Root description*.—Fibrous; white in color.

*Rooting habit*.—Freely branching.

Plant description:

*Plant and growth habit*.—Compact and mounding plant habit; freely branching habit with numerous lateral branches developing per plant; pinching enhances lateral branch development; vigorous growth habit.

*Plant height*.—About 20.7 cm.

*Plant diameter*.—About 49 cm.

Lateral branch description:

*Length*.—About 22 cm.

*Diameter*.—About 1.8 mm.

*Internode length*.—About 1.6 cm.

*Strength*.—Strong.

*Aspect*.—Upright to outwardly.

*Texture*.—Pubescent.

*Color*.—Close to 144B.

Leaf description:

*Arrangement*.—Alternate, simple.

*Length*.—About 4.14 cm.

*Width*.—About 1.25 cm.

*Shape*.—Spatulate.

*Apex*.—Obtuse.

*Base*.—Cuneate.

*Margin*.—Entire.

*Texture, upper and lower surfaces*.—Pubescent.

*Venation pattern*.—Pinnate; reticulate.

*Color*.—Developing leaves, upper surface: Close to 143A. Developing leaves, lower surface: Close to 143B. Fully expanded leaves, upper surface: Close to 137B; venation, close to 138B. Fully expanded leaves, lower surface: Close to 138B; venation, close to 138C.

*Petioles*.—Length: About 3.7 mm. Diameter: About 1.7 mm. Texture, upper and lower surfaces: Pubescent. Color, upper and lower surfaces: Close to 144C.

Flower description:

*Flower arrangement and habit*.—Single salverform flowers arising from upper leaf axils; freely flowering habit with usually about 224 flowers developing per plant; flowers face upright or outwardly.

*Fragrance*.—None detected.

*Natural flowering season*.—Early flowering habit, plants of the new *Calibrachoa* initiate and develop flowers about three to four weeks after planting; long flowering period, flowering naturally commences during the early spring and plants flower continuously throughout the summer until late autumn in Japan.

*Flower longevity*.—Individual flowers last about seven to ten days on the plant; flowers not persistent.

*Flower diameter*.—About 2.88 cm.

*Flower length (depth)*.—About 2.22 cm.

*Throat diameter*.—About 7.4 mm.

*Tube length*.—About 1.62 cm.

*Tube diameter, base*.—About 2.9 mm.

*Flower buds*.—Shape: Cylindrical. Length: About 1.96 cm. Diameter: About 5.2 mm. Color: Close to 4C.

*Corolla*.—Arrangement: Five petals fused at the base and opening into a flared trumpet. Petal length from throat: About 1.2 cm. Petal width: About 1.37 cm. Petal shape: Roughly spatulate. Petal apex: Rounded, slightly retuse. Petal margin: Entire. Petal texture, upper and lower surfaces: Smooth, glabrous. Throat texture: Smooth, glabrous. Tube texture: Pubescent. Color: Petal, when opening and fully opened, upper surface: Close to NN155D; venation, close to N144B, faint. Petal, when opening and fully opened, lower surface: Close to NN155D; venation, close to NN155D. Throat: Close to 5B; venation, close to 5B. Tube: Close to 3C; venation, close to 3C.

*Calyx*.—Arrangement: One star-shaped tubular calyx tube with five sepals fused at the base. Sepal length: About 6.3 mm to 9.5 mm. Sepal width: About 2.8 mm. Sepal shape: Lanceolate. Sepal apex: Obtuse. Sepal margin: Entire. Sepal texture, upper and lower surfaces: Pubescent. Sepal color: Immature and mature, upper surface: Close to 138A. Immature and mature, lower surface: Close to 138B.

*Peduncles*.—Length: About 1.7 cm. Diameter: About 0.7 mm. Angle: Upright to outwardly. Strength: Strong. Texture: Pubescent. Color: Close to 144A.

*Reproductive organs*.—Stamens: Quantity: Five per flower. Stamen length: About 6.5 mm to 10.8 mm. Anther shape: Ellipsoidal. Anther size: About 1.2 mm by 1.4 mm. Anther color: Close to 12B. Pollen amount: Moderate. Pollen color: Close to 12A. Pistils: Quantity: One per flower. Pistil length: About 9.6 mm. Style color: Close to 144D. Stigma shape: Transversely ellipsoidal. Stigma color: Close to 144B. Ovary color: Close to 144B.

*Seeds and fruits*.—Seed and fruit development have not been observed on plants of the new *Calibrachoa*.

Garden performance: Plants of the new *Calibrachoa* have been observed to have good garden performance and to tolerate wind, rain and temperatures ranging from about 5° C. to about 35° C.

Pathogen & pest resistance: Plants of the new *Calibrachoa* have not been observed to be resistant to pests and pathogens common to *Calibrachoa* plants.

It is claimed:

1. A new and distinct *Calibrachoa* plant named 'Sunbel 789' as illustrated and described.

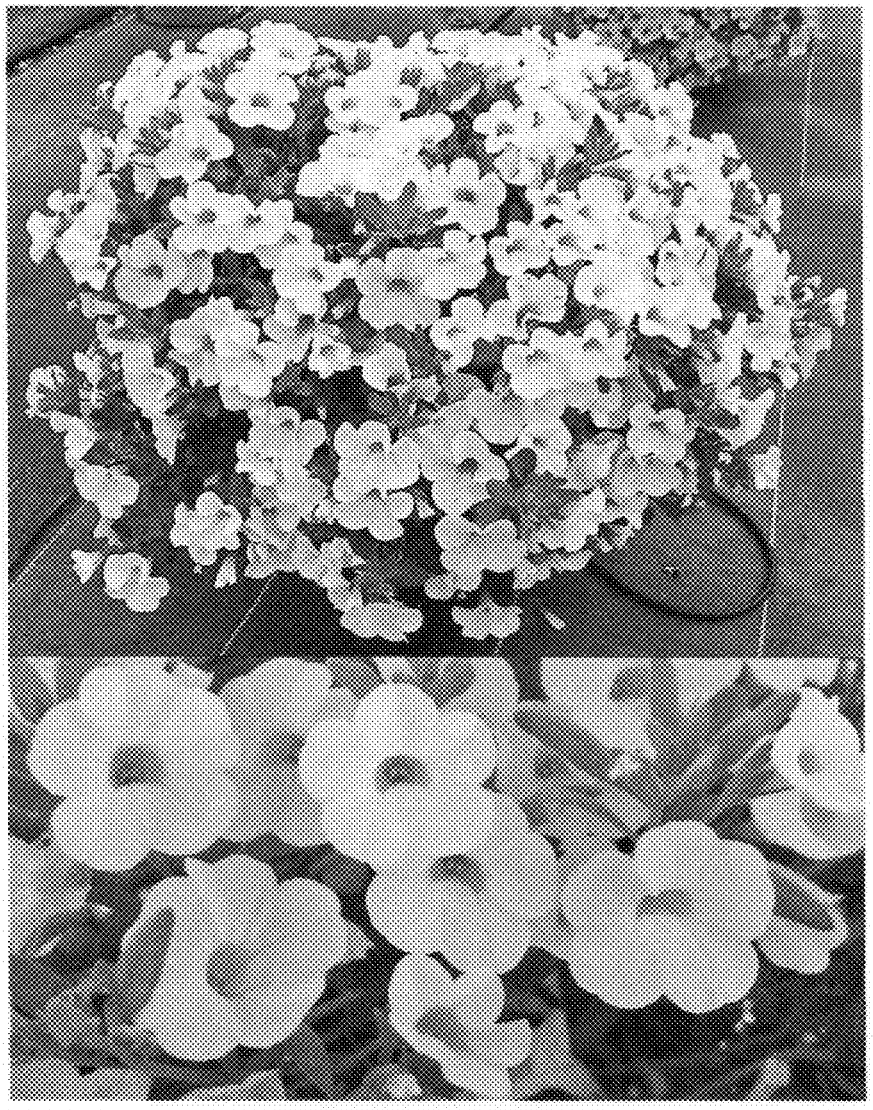

* * * * *